(12) United States Patent
Sitther et al.

(10) Patent No.: US 12,331,336 B2
(45) Date of Patent: Jun. 17, 2025

(54) ENGINEERED CYANOBACTERIA WITH ENHANCED UV TOLERANCE

(71) Applicant: Morgan State University, Baltimore, MD (US)

(72) Inventors: Viji Sitther, Pikesville, MD (US); Samson Gichuki, Nottingham, MD (US)

(73) Assignee: Morgan State University, Baltimore, MD (US)

( * ) Notice: Subject to any disclaimer, the term of this patent is extended or adjusted under 35 U.S.C. 154(b) by 0 days.

(21) Appl. No.: 17/891,482

(22) Filed: Aug. 19, 2022

(65) Prior Publication Data

US 2023/0340502 A1    Oct. 26, 2023

Related U.S. Application Data

(60) Provisional application No. 63/246,383, filed on Sep. 21, 2021, provisional application No. 63/234,895, filed on Aug. 19, 2021.

(51) Int. Cl.

| | | |
|---|---|---|
| *C12N 9/88* | (2006.01) | |
| *C12N 1/20* | (2006.01) | |
| *C12N 15/74* | (2006.01) | |
| *C12P 7/649* | (2022.01) | |
| *C12R 1/01* | (2006.01) | |

(52) U.S. Cl.
CPC ............... *C12N 9/88* (2013.01); *C12N 1/205* (2021.05); *C12N 15/74* (2013.01); *C12P 7/649* (2013.01); *C12R 2001/01* (2021.05)

(58) Field of Classification Search
CPC ...................................................... C12N 9/88
See application file for complete search history.

(56) References Cited

U.S. PATENT DOCUMENTS

2019/0071699 A1*    3/2019    Sitther ................. C12P 7/6458

OTHER PUBLICATIONS

MW357071. GenBank Database. Feb. 16, 2021.*
Ng (PhrA, the major photoreactivating factor in the cyanobacterium *Synechocystis* sp. strain PCC 6803 codes for a cyclobutane-pyrimidine-dimer-specific DNA photolyase. Arch Microbiol. May-Jun. 2000; 173(5-6):412-7.*
Fransceus. J Ind Microbiol Biotechnol. May 2017;44(4-5):687-695.*
Sanavia. Computational and Structural Biotechnology Journal, vol. 18, 2020, pp. 1968-1979.*
Gichuki. Augmentation of the Photoreactivation Gene in Fremyella diplosiphon Confers UV-B Tolerance. ACS Omega. Sep. 23, 2022;7(39):35092-35101.*

* cited by examiner

*Primary Examiner* — Yong D Pak
(74) *Attorney, Agent, or Firm* — Whiteford, Taylor & Preston, LLP; Peter J. Davis

(57) ABSTRACT

A recombinant strain of *F. diplosiphon* was made by transforming wild type *F. diplosiphon* with a pGEM-7Zf (+) plasmid containing the photolyase gene (phrA) via electroporation. The recombinant strain was designated B481-ViAnSa and overexpressed the phrA gene to result in enhanced UV tolerance compared to wild type *F. diplosiphon*.

3 Claims, 13 Drawing Sheets

Specification includes a Sequence Listing.

FIGURE 1

SEQUENCE LISTING

```
Sequence total quantity: 4
SEQ ID NO: 1            moltype = DNA   length = 27
FEATURE                 Location/Qualifiers
source                  1..27
                        mol_type = unassigned DNA
                        organism = Fremyella diplosiphon
SEQUENCE: 1
aagctttatg tggcacacga ctgtacc                                    27

SEQ ID NO: 2            moltype = DNA   length = 28
FEATURE                 Location/Qualifiers
source                  1..28
                        mol_type = unassigned DNA
                        organism = Fremyella diplosiphon
SEQUENCE: 2
ggatccggtt atttgaccaa ttgataac                                   28

SEQ ID NO: 3            moltype = DNA   length = 1432
FEATURE                 Location/Qualifiers
source                  1..1432
                        mol_type = genomic DNA
                        organism = Fremyella diplosiphon
```

```
SEQUENCE: 3
ctagctttt  tgctgttgat  aaatttgttt  aaagttgttg  ctgaatctta  tgatccacaa   60
tggggtcagg  ataacccacc  gcacggcgtt  ctagtggtgt  gattttacca  gttactaaat  120
attcagtatc  tatagaccgc  aattctggca  accattggcg  gatatattcg  gcatctggat  180
cgaattttg  ggcttggcta  gctgggtgga  aaccgcgtat  aggtttaggg  tccatgccac  240
tagaagcact  ccattgccaa  ccaccattat  tggcagacaa  gtccccatca  atcaatctct  300
gcataaaata  ttttttctcc  aattgcggac  tgattaataa  atctttaatc  aggaaactag  360
caacaatcat  ccgacaacga  ttatgcatcc  agccgctttc  gtttaattac  cgcatggctg  420
catcgacaat  ggggtagcct  gttctgcctt  cacaccaagc  ttgataatgt  tcttcgttgt  480
tttcccaagg  aaatcgtttg  aaggcttcgc  ggtaagcacc  ctcagctaat  tccgggaagt  540
gatacatagc  atgttgataa  aatttcccgcc  atgctagttc  ttgttgccat  gtcggatgc   600
tggttgtggt  ttcgtcgcta  cggctatttt  ctaagttttc  tagggtagtt  tgccaaacag  660
tgcgaatgcc  gatcgcgcca  aatttgaaag  ctgcactcag  ctgtgatgta  ccatcgatag  720
ccgccggaaa  attccgctgt  tcctggtatt  cattaatcgc  actagcgcta  aattcctcta  780
accttcttg  cgctgcggct  tctcctgggg  gaagaactaa  tccgccataa  aaaataatag  840
ctaaatcttt  ggcggttggt  agtggtattg  ctccagtttg  ctgggcaatt  tcttgttcaa  900
tagctgttaa  cccttcggca  ttttgcagag  tttctcgggg  tttagctttg  ggtttgctaa  960
tccaattttt  ccagaagggg  gtataaacag  tgtaagggcc  attaccacct  gtacgaattt 1020
ctgctggtga  gtgcagtatc  tgatcccagt  tttctgctaa  aaatgcaatg  ccttttttctt 1080
ggagcgcatc  aattatagtg  cgatcgcgtt  cttgagaata  gggttctaca  tcccagttcc 1140
aaaataccgc  ttttgcattt  aacgccgtag  ctaaggcggg  aattgcttgc  atgggattac 1200
catgaactat  taacaactgg  ctaccagctt  ccgcataggcg  aggttgtaat  gcttgtaagc 1260
agccaatcat  ataagttacc  cgcaccgagc  aaatatcatc  ccgttggaga  atattcgggt 1320
cgaggcaaag  tactcctact  accttaggac  tttgcccgcg  ggctgcggct  agtcctgtat 1380
tatcagaaat  ccttaaatcg  cggcgatgcc  aaaatagaat  tatgacagag  ca         1432

SEQ ID NO: 4          moltype = DNA  length = 1434
FEATURE               Location/Qualifiers
source                1..1434
                      mol_type = genomic DNA
                      organism = Fremyella diplosiphon
SEQUENCE: 4
ctagctttt  tgctgttgat  aaatttgttt  aaactgttgt  tgctgaatct  tatgatccac   60
aatggggtca  ggataaccca  ccgcacggcg  ttctagtggt  gtgattttac  cagttactaa  120
atattcagta  tctatagacc  gcaattctgg  caaccattgg  cggatatatt  cggcatctgg  180
atcgaattt  tgggcttggc  tagctgggtt  gaaaatgcgt  ataggtttag  ggtccatgcc  240
actagaagca  ctccattgcc  aaccaccatt  attggcagat  aagtcccat  caatcaatct   300
ctgcataaaa  tattttctc  ccaattgcgg  actgattaat  aaatctttag  tcaggaaact  360
agcaacaatc  atccgacaac  gattatgcat  ccagccgctt  tcgtttaatt  ggcgcatggc  420
tgcatcgaca  atggggtagc  ctgttctgcc  ttcacaccaa  gcttgataat  gttcttcgtt  480
gttttcccaa  ggaaagcttt  tgaaggcttc  gcggtaagca  ccctcagcta  attccgggaa  540
gtgatacata  gcatgttgat  aaaattcccg  ccatgctagt  tcttgttgcc  atgtgcggat  600
gctggttgtg  gtttcgtcgc  tacggctatt  ttctagcgtt  tctagggtag  tttgccaaac  660
agtgcgaatg  ccgatcgcgc  caaatttgaa  agctgcactc  agctgtgatg  taccatcgat  720
agccgccgga  aaattccgct  gttcctggta  ttcattaatc  gcactagcgc  taaattcctc  780
taacctttct  tgcgctgcgg  cttctcctgg  gggaagaact  aatccgccat  cccaaataat  840
tcctaaatct  ttggcggttg  gtagtggtat  tgctccagtt  tgctgggcaa  tttcttgttc  900
aatagctgtt  aacccttcgg  catttttgcag  agttttctact  ggtttagctt  tgggtttgct  960
aatccaattt  ttccagaagg  gggtataaac  agtgtaaggg  gcattaccac  ctgtacgaat 1020
ttctgctggt  gagtgcagta  tctgatccca  gttttctgct  aaaaatgcaa  tgccttttc 1080
ttggagcgca  tcaattatag  tgcgatcgcg  ttcttgagaa  tagggttcta  catcccagtt 1140
ccaaaatacc  gctttggcat  ttaacgccgt  agctaaggcg  ggaattgctt  gcatgggatt 1200
accatgaact  attaacaact  ggctaccagc  ttccgcatag  cgcttttgta  atgcttgtaa 1260
gcagccaatc  atataagtta  cccgcaccga  ggaaatatca  tcccgttgga  gaatattcgg 1320
gtcgaggcaa  aatactccta  ctaccttagg  actttgtttg  cgggctgcgg  ctagtcctgt 1380
attatcagaa  atccttaaat  cgcggcgatg  ccaaaataga  attaagtcag  agca       1434
```

ENGINEERED CYANOBACTERIA WITH ENHANCED UV TOLERANCE

GOVERNMENT RIGHTS STATEMENT

This invention was made with government support under 1900966 awarded by the National Science Foundation. The government has certain rights in the invention.

BACKGROUND OF THE INVENTION

Reference to Sequence Listing

This application includes a Sequence Listing XML file named "2023-05-15SequenceListing.xml", 8,000 bytes in size and created May 15, 2023, which is hereby incorporated by reference.

FIELD OF THE INVENTION

The present invention relates to bioengineered cyanobacteria with enhanced properties.

DESCRIPTION OF THE BACKGROUND

The negative impact of fossil fuels on the environment and human health has sparked enormous interest in the development of biofuels as a renewable energy source. While cyanobacteria are an ideal third-generation feedstock for a variety of fuels including biodiesel, ethanol, and biogas, these photosynthetic organisms face an immense threat due to the global climatic changes. In recent years, a decrease in stratospheric ozone layer due to excessive release of air pollutants such as chlorofluorocarbons, organobromides, and reactive nitrogen species has resulted in increased solar UV-B (280-320 nm) reaching the Earth's surface. Several physiological and biochemical processes such as motility, photo-orientation, and $CO_2$ uptake in cyanobacteria are impaired by UV radiation. In addition, it is known to adversely impact biomolecules in these organisms, with nucleic acids being the primary targets.

Studies by Rastogi et al. and Castenholz & Garcia-Pichel have reported that cyanobacterial genomic function and fidelity are adversely affected by UV-B, as the DNA molecules directly absorb UV-B radiation inducing DNA strand breaks. A variety of mutagenic and cytotoxic DNA lesions including cyclobutane-pyrimidine dimers (CPDs), 6-4 photoproducts (6-4PPs), and their Dewar valence isomers are induced, disrupting genomic integrity. In addition, cyanobacterial UV-B induced-DNA degradation due to thymine dimerization has been confirmed in *Anabaena, Nostoc,* and *Scytonema* sp. Additionally, UV-B-induced DNA lesions (CPDs and 6-4PPs) can also cause primary and secondary breaks, since they are associated with transcription and replication blockages, leading to the collapse of replication forks in CPD-containing DNA.

To combat the negative effects of radiation stress, cyanobacteria employ a variety of direct and indirect defense strategies that enable tolerance to fluctuating UV levels. The first line of defense employed by most cyanobacterial species is the avoidance by migration through self-shading or mat formation. Cyanobacteria such as *Anabaena* sp. *Nostoc-commune* and *Scytonema* sp. have the capacity to produce UV-absorbing compounds mycosporine-like amino acids and scytonemin as a response to UV radiation. Although cyanobacteria use these defense mechanisms to combat UV stress, these repair systems can be rapidly overwhelmed by sustained UV radiation. However, some species employ photoreactivation, a process in which photolyase is activated by the blue wavelength of solar light, to reverse and modify nitrogenous bases to their normal state followed by thymine dimer formation caused by UV radiation.

*Fremyella diplosiphon* is a well-studied cyanobacterial species that has great potential as a third-generation biofuel agent due to its fatty acid methyl esters. In addition to growth in varying light intensities by modifications of its light-harvesting complexes, the organism is extremely amenable to genetic transformation. Efforts to enhance value-added traits such as halotolerance and cellular lipid content in this species have enabled unique environmental applications. A report by Vass et al. has indicated that phr A gene plays a role in DNA repair mechanism of *Synechocystis* sp. PCC 6803, and mutant cells lacking the gene were highly susceptible to UV-B damage.

SUMMARY OF THE INVENTION

The development of a UV-B tolerant strain would be invaluable to maximize its potential for biofuel production in scale-up systems. An object of the present invention was to overexpress the photoreactivation (phr A) gene in *F. diplosiphon* B481-WT to enhance UV-B tolerance. Successful transformation was confirmed using RT-qPCR and fluorometric analysis of DNA unwinding assays, and photosynthetic efficiency evaluated as a measure of photosystem II functionality, which is known to be adversely impacted by UV-B. Additionally, fatty acid methyl ester (FAME) profile of the transformant compared favorably to the wildtype, confirming its usefulness as a biofuel.

BRIEF DESCRIPTION OF THE DRAWINGS

The foregoing summary, as well as the following detailed description of the preferred invention, will be better understood when read in conjunction with the appended figures. In the figures:

FIG. 1 shows the basic local alignment search tool analysis of *F. diplosiphon* B481-WT photolyase gene (SEQ.ID.NO. 3) on the National Center for Biotechnology Information showing 97.82% similarity to the photolyase gene in *Nostoc* sp (SEQ.ID.NO. 4).

DETAILED DESCRIPTION OF THE INVENTION

Figure 2A:
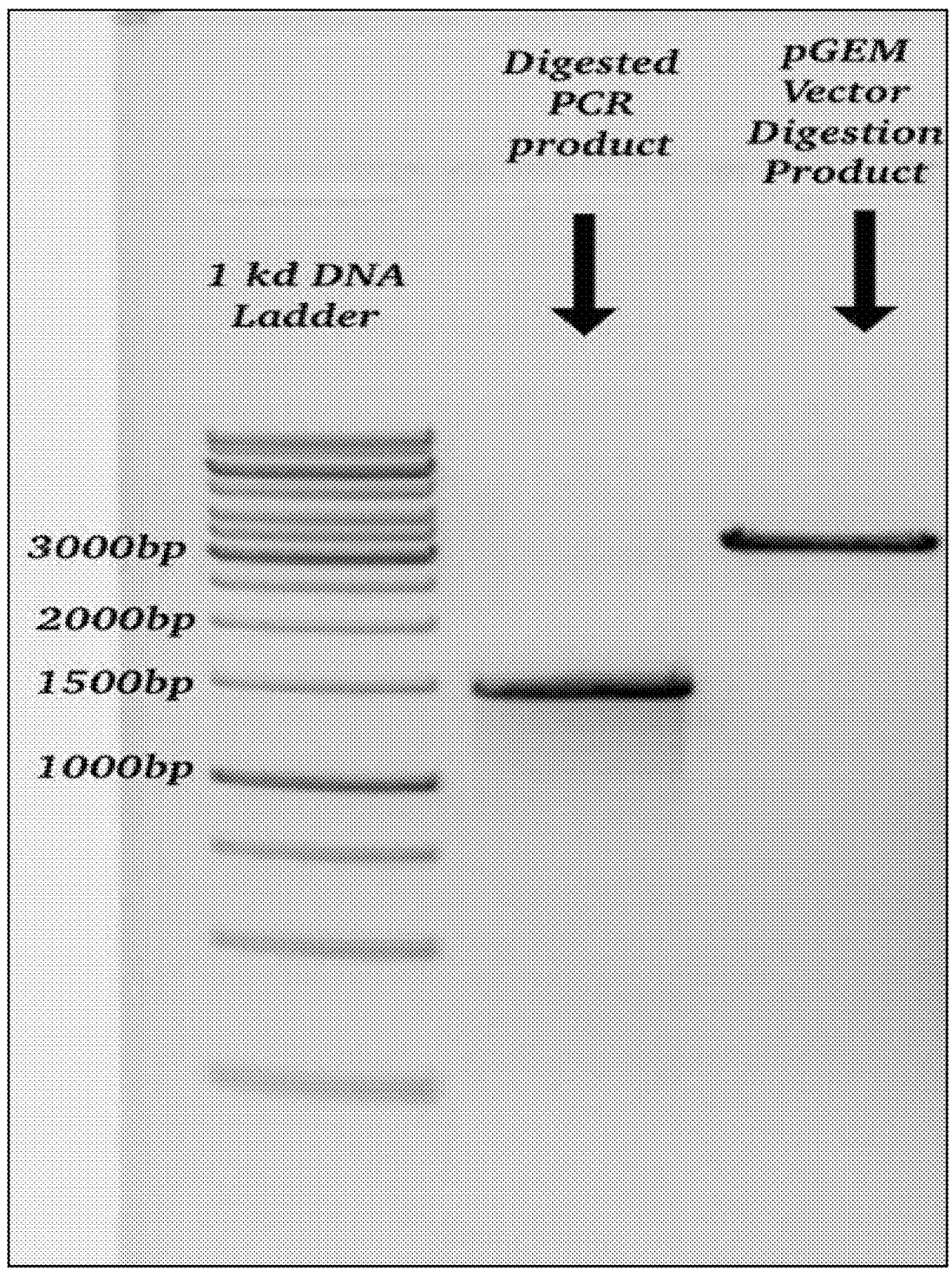
FIG. 2A shows an electrophoresis gel of polymerase chain reaction of amplification product of double digested photoreactivation gene from extracted vector in lane 2 and pGEM-7Zf vector in lane 3.

To enhance UV stress tolerance in this species, we overexpressed the photoreactivation gene (phrA) that encodes for photolyase DNA repair enzyme in the wild type *F. diplosiphon* (B481-WT) by genetic transformation. Our efforts resulted in a transformant (B481-ViAnSa) with a 3,808-fold increase in the phrA mRNA transcript level, with enhanced growth under UVB stress. Additionally, DNA strand breaks in the transformant were significantly lower after 12 and 16 h of UV radiation, with significantly higher dsDNA recovery in B481-ViAnSa (98.1%) compared to B481-WT (81.5%) at 48 h post irradiation. Photosystem II recovery time in the transformant was significantly reduced (48 h) compared to the wildtype (72 h). Evaluation of high-value fatty acid methyl esters (FAMEs) revealed methyl palmitate, the methyl ester of hexadecenoic acid (C16:0), to be the most dominant component, accounting for 53.43% of the identified FAMEs in the transformant. The present invention thus presents an increased UV tolerant recombinant *Fremyella diplosiphon* and a method for enhancing UV tolerance in cyanobacteria, thus paving the way to large-scale open or closed pond cultivation for commercial biofuel production.

Materials and Methods

Strains and Culture Conditions

*F. diplosiphon* strain (B481-WT) obtained from the UTEX algal repository (Austin, USA) was grown in liquid BG-11 medium containing 20 mM HEPES (hereafter termed as BG-11/HEPES) to an exponential growth phase (optical density at 750 nm of ~0.6). Cultures were grown under continuous shaking at 170 rpm and 28° C. in an Innova 44R incubator shaker (Eppendorf, Germany). The photosynthetic light in the shaker had peak wavelengths at 437 nm and 600-650 nm with an intensity adjusted to 30 mol m$^{-2}$ s$^{-1}$ using the model LI-190SA quantum sensor (Li-Cor, USA).

RNA Isolation and Complementary DNA Synthesis

Total RNA was extracted from *F. diplosiphon* grown to an exponential phase (7 days) using Tri Reagent (Molecular Research Center, Inc.) according to the manufacturer's protocol with modifications. The concentration and purity of the extracted RNA was tested on an agarose gel and A260/280 absorbance ratio measured using a Nanodrop 2000 (Thermo Fisher Scientific, USA). Complementary DNA (cDNA) was synthesized using the high-capacity RNA to cDNA kit (Life Technologies, USA). A 20 μl reaction mixture containing 1000 ng of RNA, 2× reverse transcription buffer (RT), and 10× RT random primers was incubated at 37° C. for 60 min followed by 95° C. for 5 min. Synthesized cDNA was aliquoted and stored at −20° C.

Identification and Cloning of the Photoreactivation Gene

To identify homologs of the phr A gene in B481-WT, the forward (5'AAGCTTTATGTGGCACACGACTGTACC3') (SEQ ID NO. 1) and reverse (5'GGATCCGGTTATTTGAC-CAATTGATAAC3') (SEQ ID NO. 2) primers with EcoR1 and BamHI restriction sites were designed. Complementary DNA synthesized as described above was used as template for phr A gene amplification. PCR conditions were set in a C1000 Touch thermocycler (Bio-Rad, USA) as follows: 95° C. for 2 min; 40 cycles at 95° C. for 30 s and an annealing temperature of 51.4° C. for 30 s, followed by a final elongation step at 72° C. for 45 s. Amplified products were electrophoresed on a 1.5% agarose gel, bands excised at the expected size ranges, and DNA extracted using the gel recovery mini pre-kit (Zymo Research, USA).

The amplified gene products and pGEM-7Zf vector containing T7 promoter were double digested with EcoR1 and BamHI restriction enzymes (Promega, USA), and purified using Zymo DNA clean and concentrator kit. Inserts were ligated into the vector at the digested restriction sites with T4 DNA ligase (New England BioLabs, USA) and pGEM-7Zf-phr A expression plasmid constructed to overexpress the photolyase gene. The ligated plasmids were transformed into *E. coli* FB5α competent cells via heat shock at 42° C. for 20 s followed by incubation on ice for 5 min. The transformed cells were plated on Luria Bertoni (LB) agar plates containing 80 mg L$^{-1}$ ampicillin and incubated for 16 h at 37° C. Twenty resistant single colonies were randomly selected, transferred to liquid LB medium containing 80 mg L$^{-1}$ ampicillin and grown at 37° C. for 16 h. Plasmids were extracted using the Zyppy plasmid miniprep kit (Zymo Research, USA) and the insert confirmed by PCR and Sanger sequencing.

Electroporation-Mediated Transformation of the Phr a Gene in *F. diplosiphon*

Expression plasmid containing the phr A gene was transformed into *F. diplosiphon* B481-WT according to parameters described by Tabatabai et al. Competent cells (40 μL) were mixed with ligated purified plasmid DNA and electroporated using a GenePulser Xcell with CE module (Bio-Rad, USA) at 200Ω resistance, 1.0 kV, and 25 μF capacitance. After incubation on ice for 20 min, the transformant was grown in BG11/HEPES liquid medium for 16 h and plated on LB agar containing 80 mg L$^{-1}$ ampicillin. To verify insertion of the phr A gene, PCR was performed using gene specific primers as mentioned above and products visualized on a 1.5% agarose gel.

Quantitation of Gene Overexpression in the Transformant by Reverse Transcription-Quantitative PCR (RT-qPCR)

Total RNA from the wildtype and the transformant were extracted, cDNA was synthesized as mentioned above, and RT-qPCR performed to quantify gene overexpression. Gene-specific primers for the phr A gene were designed and real-time amplifications performed using SYBR green master mix (Applied Biosystems, USA) in a Thermal Cycler CFX96 Real-Time machine (Bio-Rad, USA). Amplifications were performed under the following conditions: 95° C. for 20 s; and 40 cycles at 50.9° C. for 30 s. Four replicates were maintained for each treatment type and the experiment repeated. Relative quantification (RQ) data of the transformant was analyzed using the ΔCt method with CFX Manager 3.1 (Bio-Rad, USA) with the B481-WT with pGEM-7Zf vector as control. The 16S rRNA was used as the internal control and fold-change values calculated.

Detection of DNA Breakages Using Fluorometric Analysis of DNA Unwinding Assay

Fluorometric analysis of DNA unwinding (FADU) assay was performed to determine DNA breakages as described previously by Rastogi et al. *F. diplosiphon* wildtype and transformant strains were grown to logarithmic phase under culture conditions described above. Cultures were diluted to an $OD_{750\ nm}$ of 0.3 and 30 mL culture exposed to 12 and 16 h of UV-B radiation in an open petri dish. Three samples were tested in this assay: UVt-sample (exposed to UV), ds-sample (double stranded sample; not UV treated or subjected to alkaline condition), and ss-sample (subjected to alkaline condition to fully unwind the DNA).

After centrifuging 1.0 mL of each sample at 3000×g for 10 min, the pellets were washed with 1 mL of TE buffer (Tris-HCl 10 mM, EDTA 1 mM), followed by 20 μL 0.5 M EDTA and 164 μL TE buffer. The cell suspension was centrifuged at 3000×g for 10 min, and 16 μL of lysozyme (50 mg/mL) added to the pellet and incubated at 37° C. for 90 min to lyse the cell walls. To the suspension, 15 μL of 10% SDS, 10 μL of 4M NaCl, 15 μL of proteinase K (6 mg/mL), and 60 μL of TE buffer was added and incubated at 60° C. for 30 min for complete cell lysis. Finally, 300 μL of 0.1 M NaOH was added to each sample and subjected to different unwinding protocols as described below.

ss-Sample. The cell extract was sonicated for 2 min, incubated at 20° C. for 30 min, neutralized by adding 300 μL of 0.1 M HCl, and sonicated for 15 s to fully unwind dsDNA and the lowest level of background fluorescence estimated.

ds-Sample. To estimate total fluorescence, cell extract was neutralized by adding of 300 μL of 0.1 M HCl, incubated at 20° C. for 30 min, and sonicated for 15 s to prevent the unwinding of dsDNA.

UVt-Sample. Cell extract was incubated at 20° C. for 30 min under alkaline condition, neutralized by adding 300 μL of 0.1 M HCl, and sonicated for 15 s to diminish the single as well as double-stranded DNA regions. This sample set was used to estimate the UV-induced DNA breaks.

After processing each sample as mentioned above, 20 μL of 20 mM Hoechst 33258 (bisbenzimide) DNA probe in 0.6 M phosphate buffer (pH 7.6) was added and centrifuged at 10,000×g for 5 min. Fluorescence intensity of 200 μL supernatant was measured using a microplate reader (Agilent BioTek Synergy H1 Hybrid, USA) at 343 nm with emission between 380 and 550 nm. The percentage fraction (% F) of dsDNA was calculated using the formula, F=(UVt−ss)/(ds−ss)×100 where ss, ds, and UVt corresponded to fluorescence intensities of ss, ds, and UVt samples respectively.

Physiological Evaluation of the Transformant Exposed to UV-B

Evaluation of Growth and Stability

The wildtype and transformant strains were grown in liquid BG11/HEPES media to logarithmic phase under culture conditions described above. Cultures were adjusted to an $OD_{750}$ of 0.1 with BG11/HEPES media and irradiated under UV-B (3.0 W m$^{-2}$) for 0 to 160 min in a UV crosslinker (Fisher Scientific, USA). Three biological replicates were maintained, and cells not irradiated with UV-B served as control. Growth of the strains at $OD_{750}$ nm was measured for a period of 14 days. Stability of the transformant was tested on BG11/HEPES plates containing 80 mg L$^{-1}$ ampicillin for a ten day-period under culture conditions described above and exposed to UV-B for 30 min per day. Stability and presence of the gene was confirmed by RT-qPCR after 18 generations of subculture.

Evaluation of Photosynthetic Pigment Levels

Photosynthetic efficacy of the wildtype and transformant was quantified as a measure of PSII activity and chlorophyll a content, which provides an estimate of the well-being of photosynthetic cells. To allow maximal irradiation and avoid cell shadowing, cultures grown to an $OD_{750}$ n of 0.3 were placed in open petri dishes and irradiated in a UV-B crosslinker (Fisher Scientific, USA) for 60 min. Cultures were grown under conditions mentioned above for three days to allow cell recovery and PSII functionality measured after 24, 48, and 72 h using a MINI-PAM (Walz, Effeltrich, Germany) to measure minimal and maximal fluorescence yield (Fo and Fm). Based on these parameters PSII quantum yield (Fv/Fo) was calculated using the equation Fv/Fm=(Fm−Fo)/Fm. In addition, chlorophyll a (chl a) was measured at the excitation of 420 nm and emission of 680 nm using a microplate reader (Agilent BioTek Synergy H1 Hybrid, USA) and photosynthetic efficacy compared.

Characterization of Lipids in the Wildtype and Transformant *F. diplosiphon* Grown Under Simulated UV-B Conditions Lipid profile of the wildtype and transformant exposed to simulated UV-B conditions (Omaykey UV-B lamps) were compared using GC-MS. Cultures adjusted to 0.1 at $OD_{750}$ were grown in 5×7×6 containers and exposed to UV-B for 4 h each day for 15 days to simulate the sun's UV-B radiation effects. Three replicated treatments were maintained and $OD_{750}$ measured every three days for a period of 12 days and growth rate calculated. Simultaneous lipid extraction and transesterification was performed as described previously by Tabatabai et al. and fatty acid composition analyzed at the Mass Spectrometry Facility at Johns Hopkins University (Baltimore, MD) using the Shimadzu GC17A/QP5050A GC-MS systems (Shimadzu Instruments, USA). Identification of FAMEs was accomplished by comparing each GC/MS mass spectrum to the Lipid Web archived FAME spectra.

Statistical Analysis

Statistical significance was determined using one-way analysis of variance (ANOVA) and Tukey's honest significant differences post-hoc test at 95% confidence intervals ($p<0.05$). The single factor, fixed-effect ANOVA model, $Y_{ij}=\mu+\alpha G_i+\varepsilon_{ij}$, was used where Y is the variable being measured in strain I and biological replicate j. The μ represents mean growth with adjustments from the effects of strain ($\alpha G$), and $\varepsilon_{ij}$ is the experimental error from strain I and biological replicate j.

Results and Discussion
Identification, Cloning, and Expression of Photolyase Phr A Gene in *F. diplosiphon*

Figure 2B:
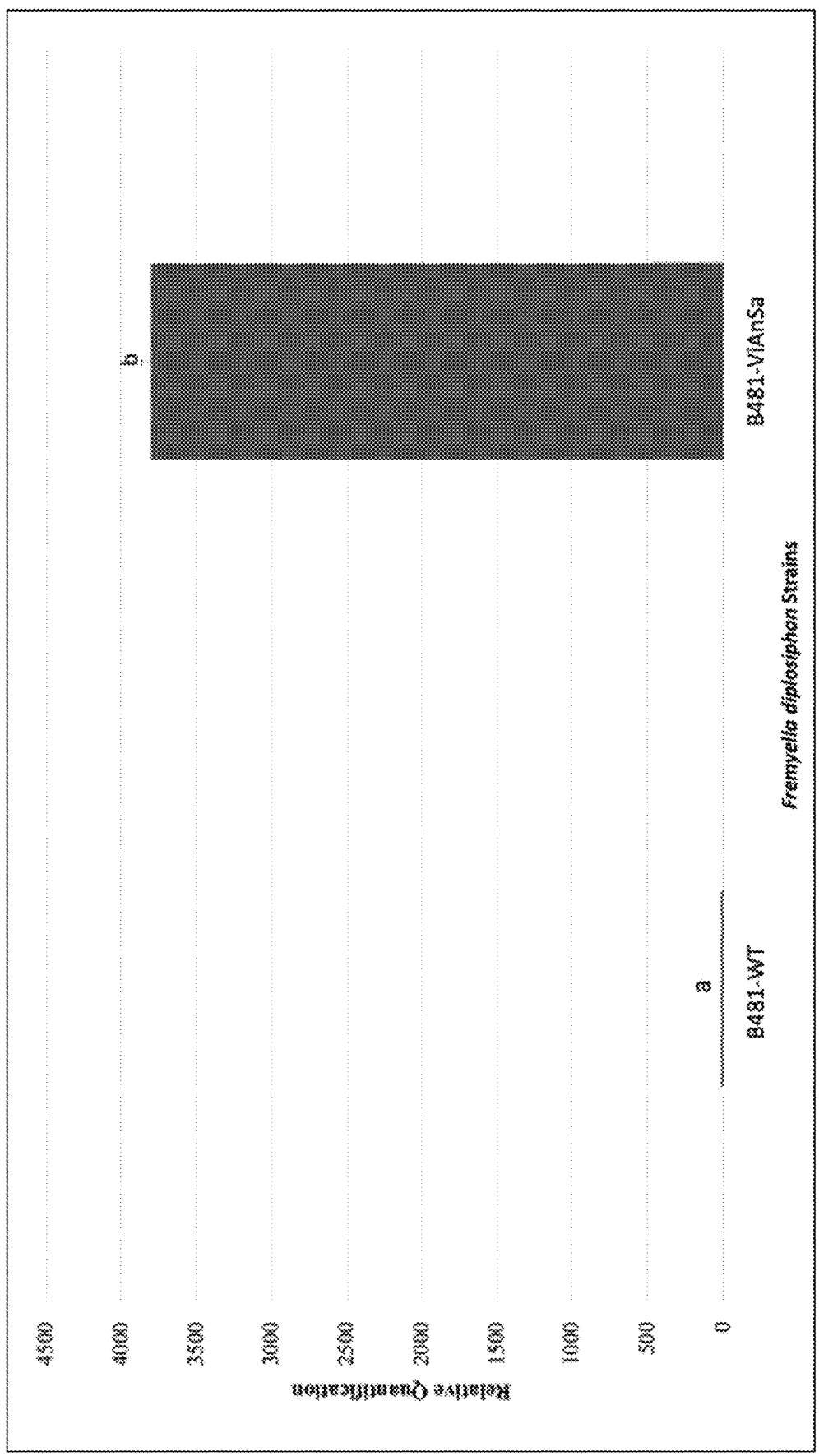
FIG. 2B is a chart showing quantification of photolyase transcript levels in *F. diplosiphon* wild type (B481-WT) and transformant (B481-ViAnSa). Error bars indicate ΔCt values at a 95% confidence interval across four replicates.
Figure 3A:
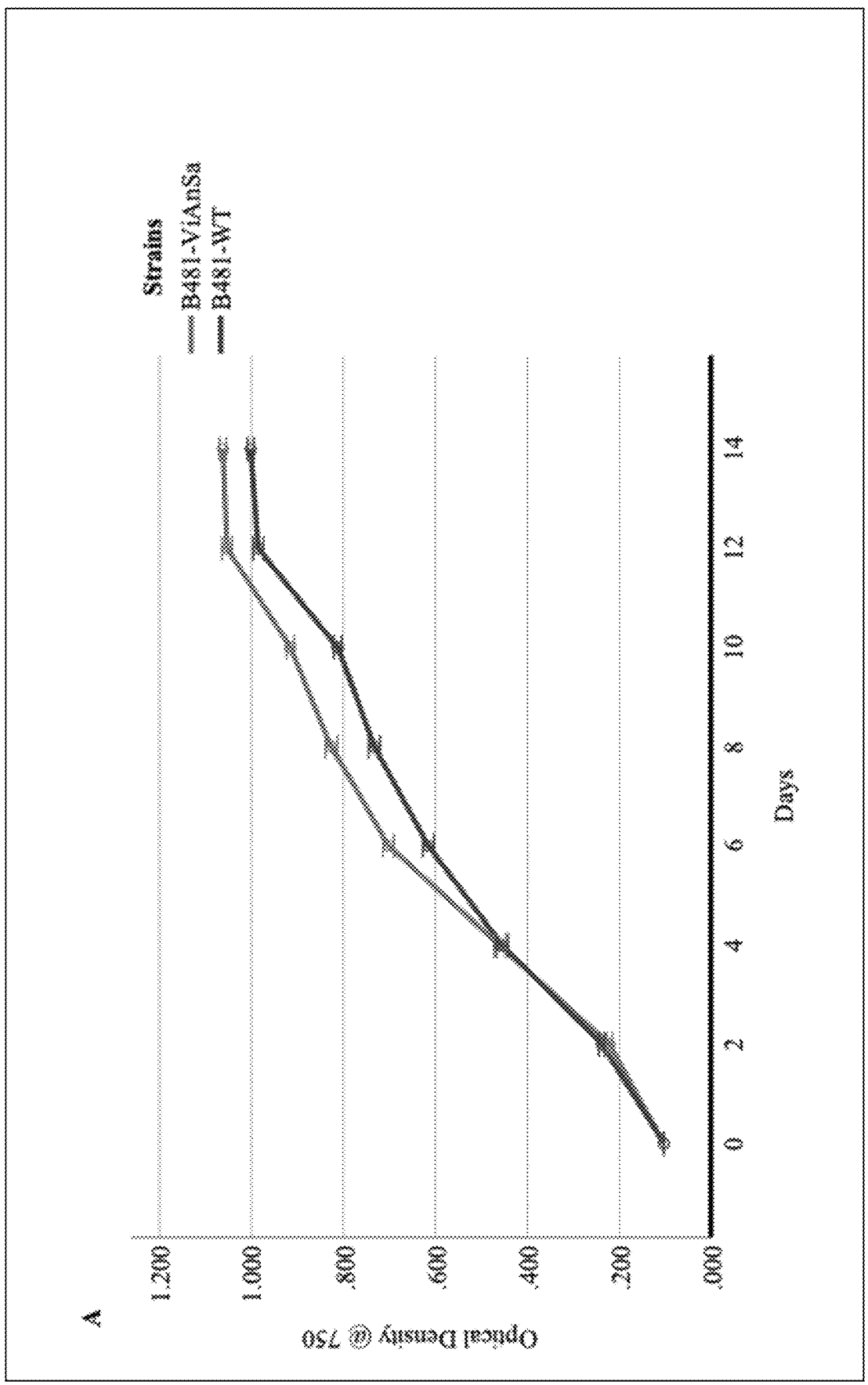
FIG. 3A is a chart showing growth of *F. diplosiphon* wild type (B481-WT) and transformant (B481-ViAnSa) strains irradiated under UVB (3.0 W m$^{-2}$) for 0 min and grown in BG11/HEPES media. Different letters above final time point indicate significance among treatment means (P<0.05).
Figure 3B:
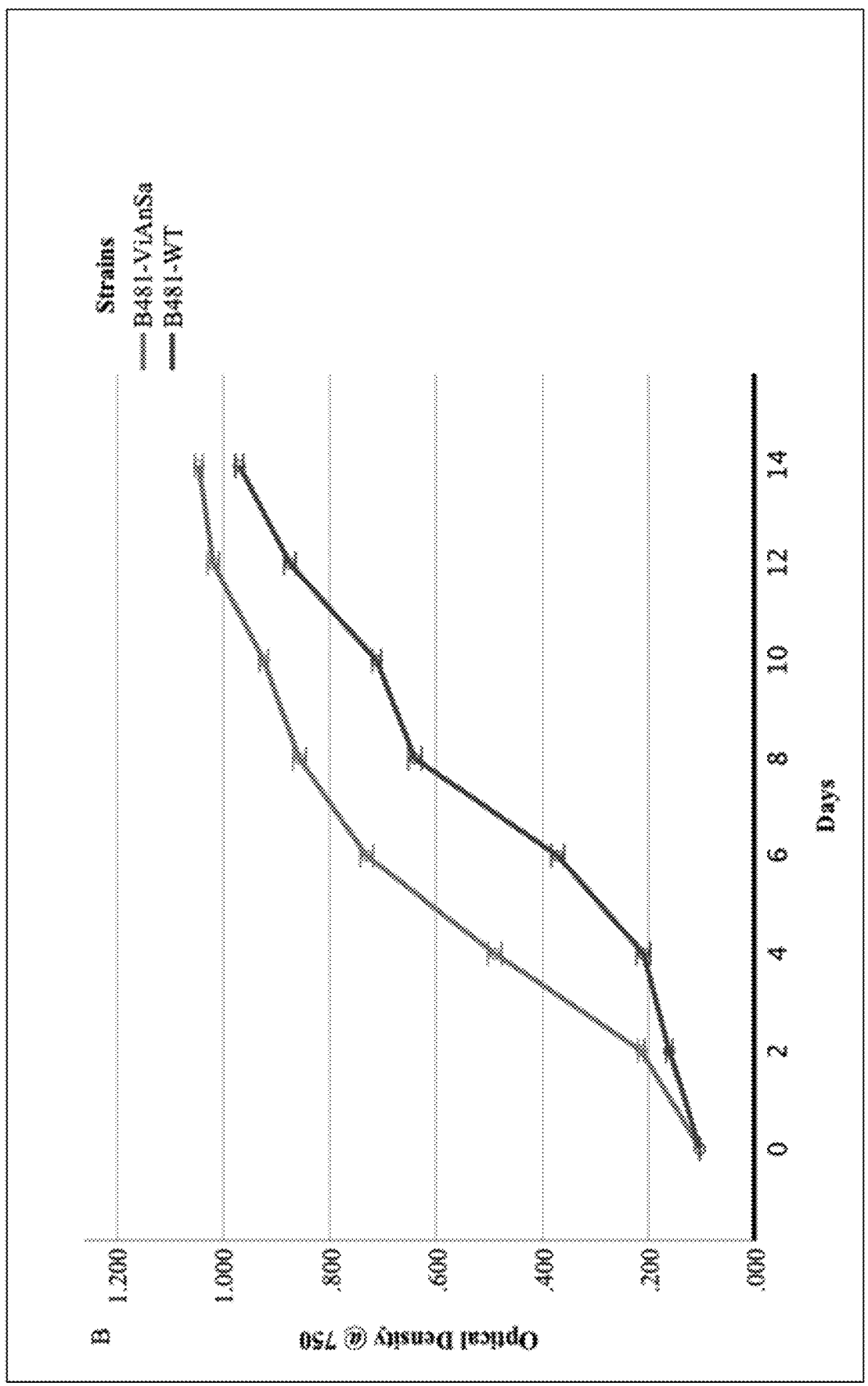
FIG. 3B is a chart showing growth of *F. diplosiphon* wild type (B481-WT) and transformant (B481-ViAnSa) strains irradiated under UVB (3.0 W m$^{-2}$) for 20 min and grown in BG11/HEPES media. Different letters above final time point indicate significance among treatment means (P<0.05).
Figure 3C:
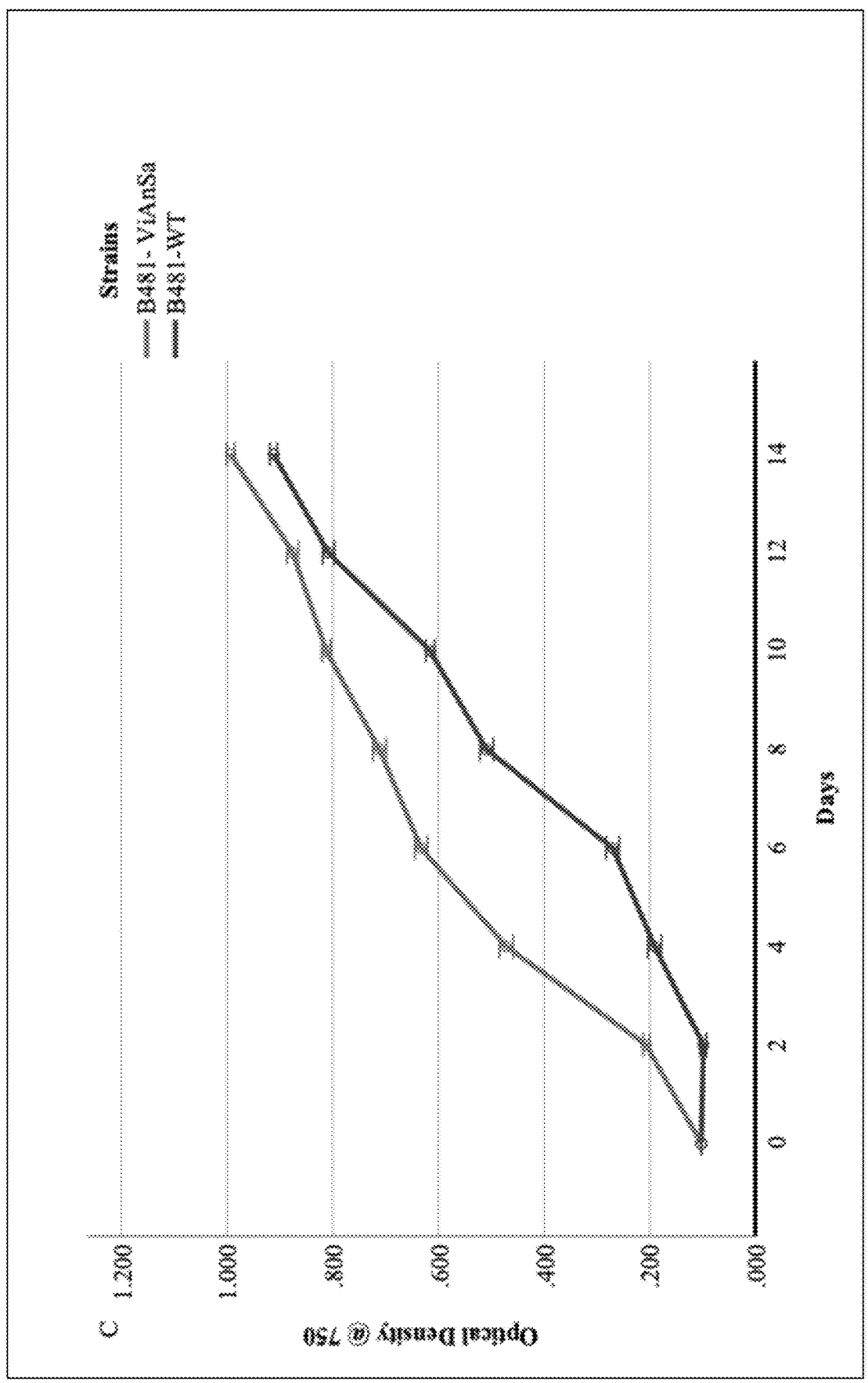
FIG. 3C is a chart showing growth of *F. diplosiphon* wild type (B481-WT) and transformant (B481-ViAnSa) strains irradiated under UVB (3.0 W m$^{-2}$) for 40 min and grown in BG11/HEPES media. Different letters above final time point indicate significance among treatment means (P<0.05).
Figure 3D:
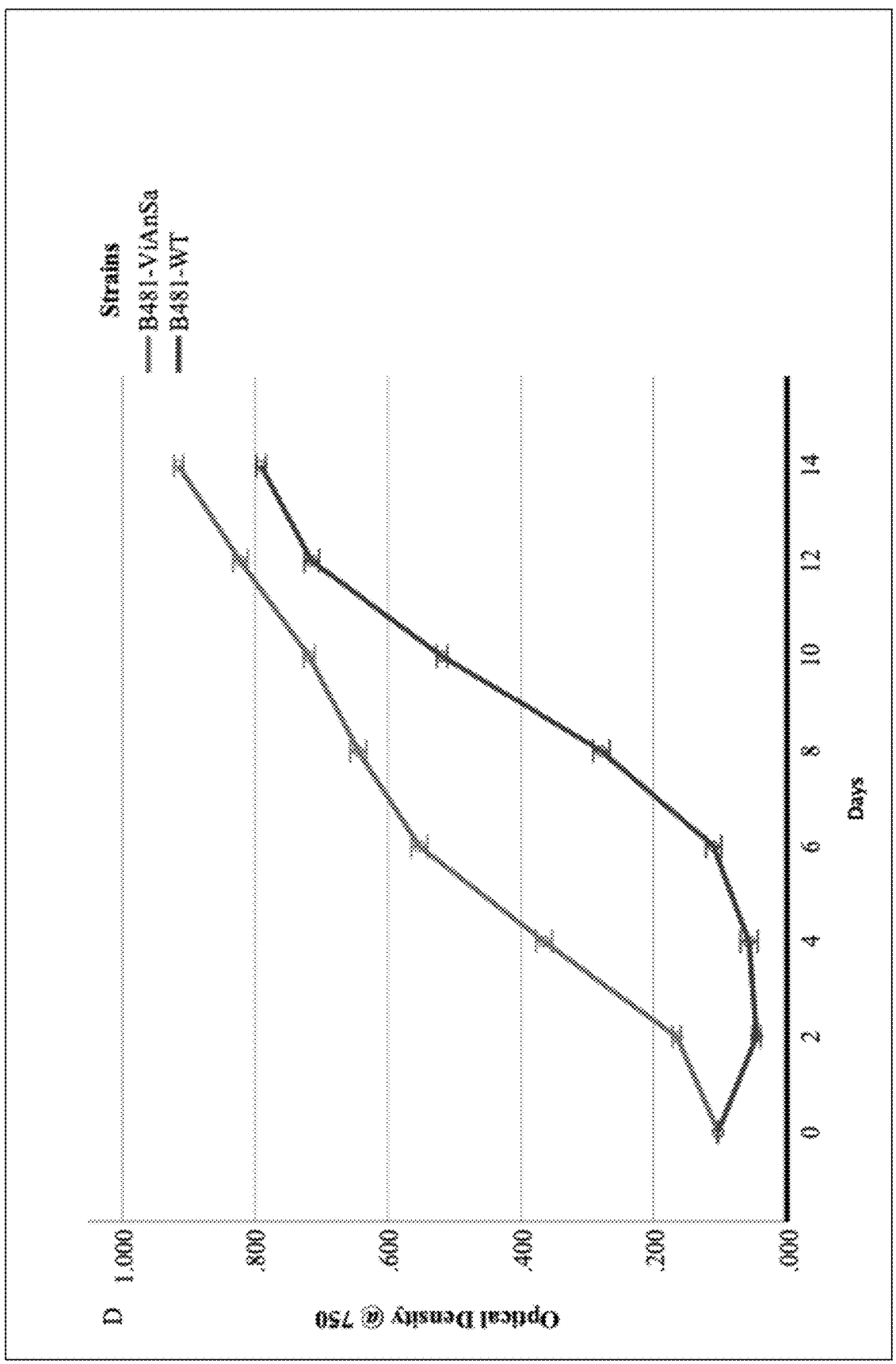
FIG. 3D is a chart showing growth of *F. diplosiphon* wild type (B481-WT) and transformant (B481-ViAnSa) strains irradiated under UVB (3.0 W m$^{-2}$) for 80 min and grown in BG11/HEPES media. Different letters above final time point indicate significance among treatment means (P<0.05).
Figure 3E:
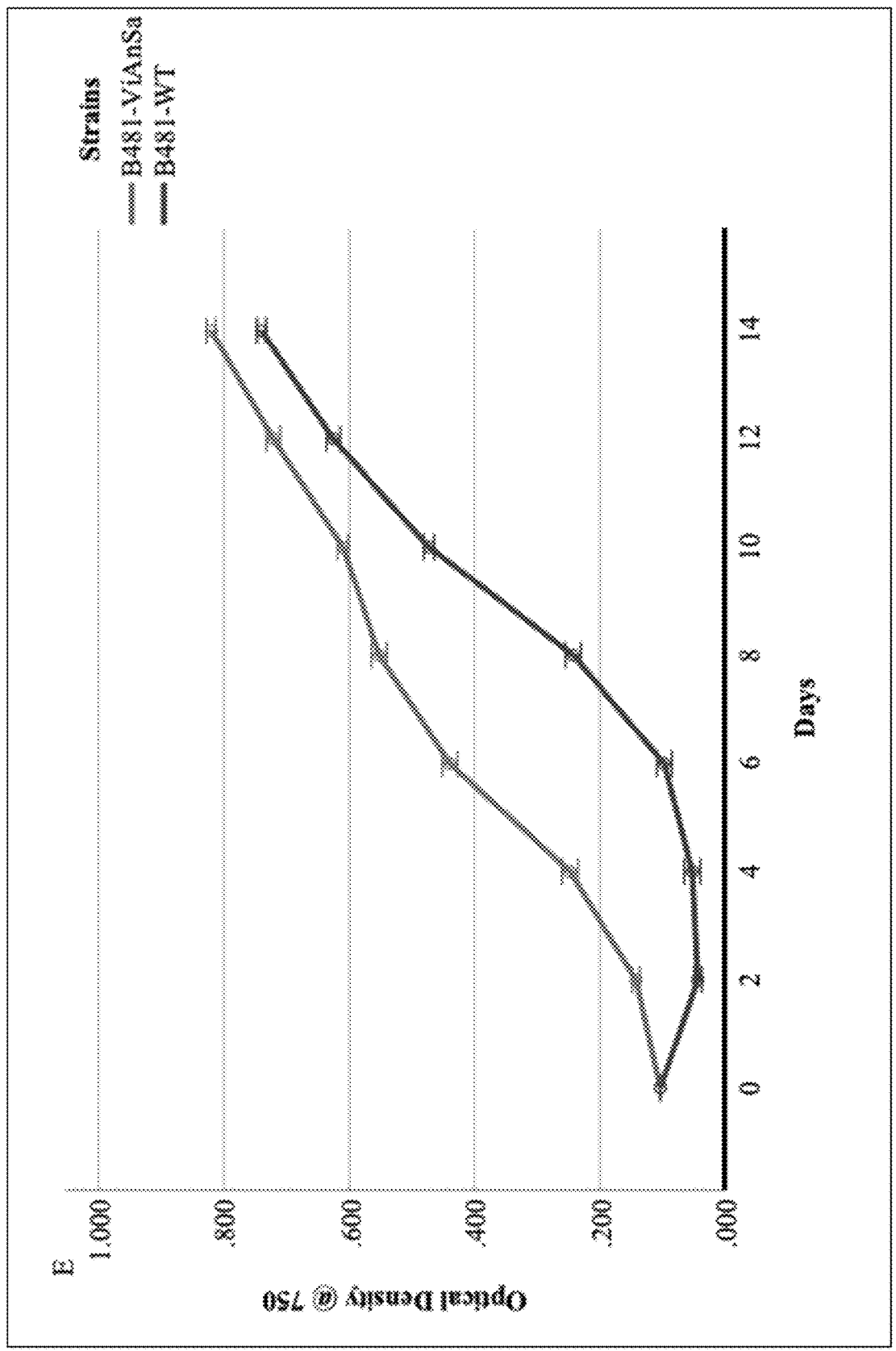
FIG. 3E is a chart showing growth of *F. diplosiphon* wild type (B481-WT) and transformant (B481-ViAnSa) strains irradiated under UVB (3.0 W m$^{-2}$) for 160 min and grown in BG11/HEPES media. Different letters above final time point indicate significance among treatment means (P<0.05).

*F. diplosiphon* UV-B tolerance was enhanced by taking advantage of the gene expression system of a plasmid vector containing the photolyase gene. Gel electrophoresis of the double digested vector construct revealed bands at the expected sizes of ~1,500 bp and ~3,000 bp for phr A gene and pGEM-7Zf plasmid respectively (FIG. 2A). The high similarity of 97.82% to the phr A gene from B481-WT (SEQ.ID.NO. 3) indicated homology to the photolyase gene in *Nostoc* sp (SEQ.ID.NO. 4). (FIG. 1). Quantification of the phr A gene transcript levels in the transformant revealed a 3,808-fold increase ($p<0.05$) compared to the wildtype strain (FIG. 2B). The phr A-overexpressing *F. diplosiphon* strain was designated as B481-ViAnSa and the sequences deposited at NCBI Genbank with the accession number MW357071.

Figure 5A:
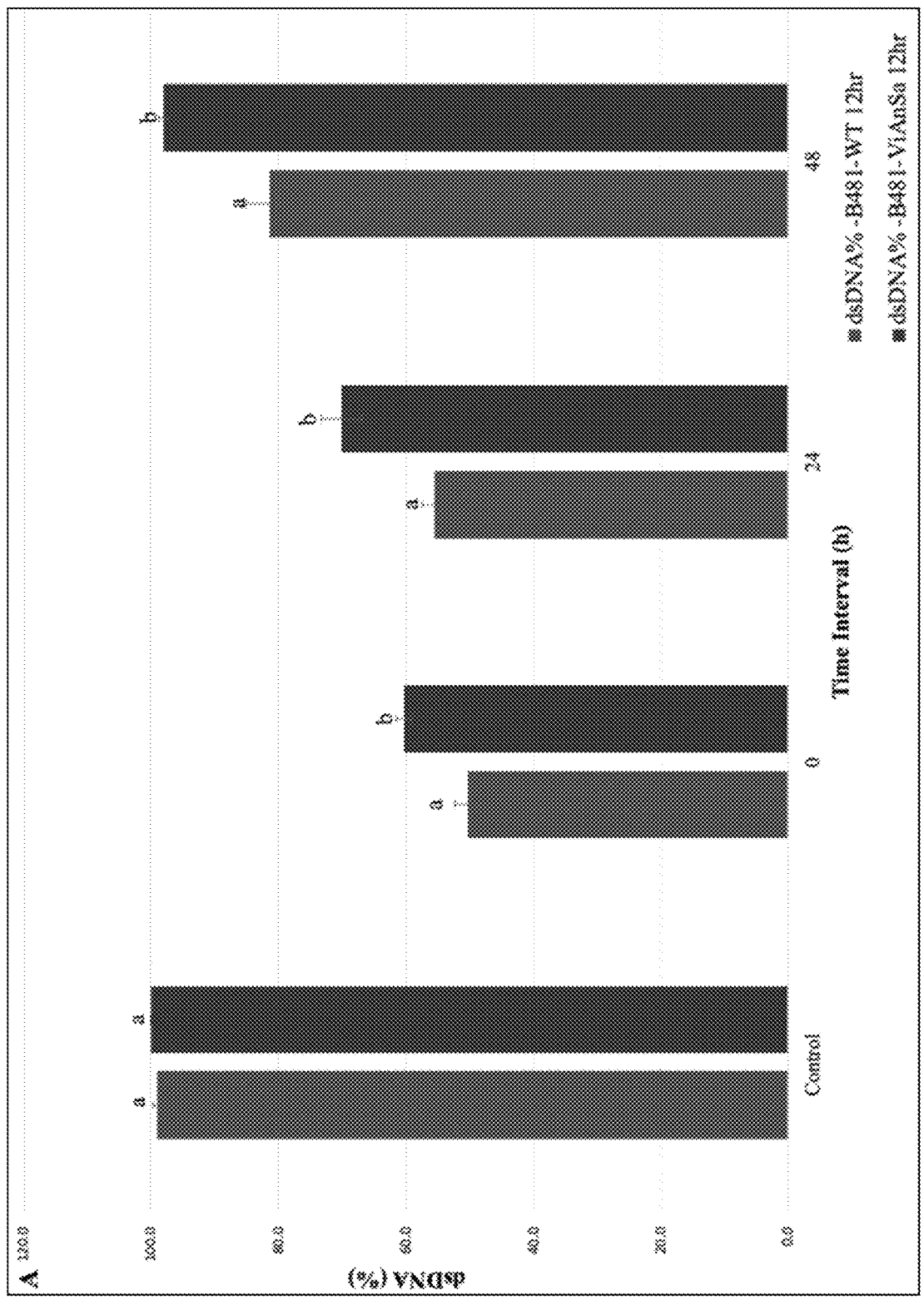
FIG. 5A is a chart showing percentages of double stranded DNA in *F. diplosiphon* wild type (B481-WT) and transformant (B481-ViAnSa) strains after exposure to UVB radiation (3.0 W m$^{-2}$ (~8.0 μmol m$^{-2}$s$^{-1}$)) for 12 h. Different letters above standard error bars indicate significance between percentages (p<0.05).
Figure 5B:
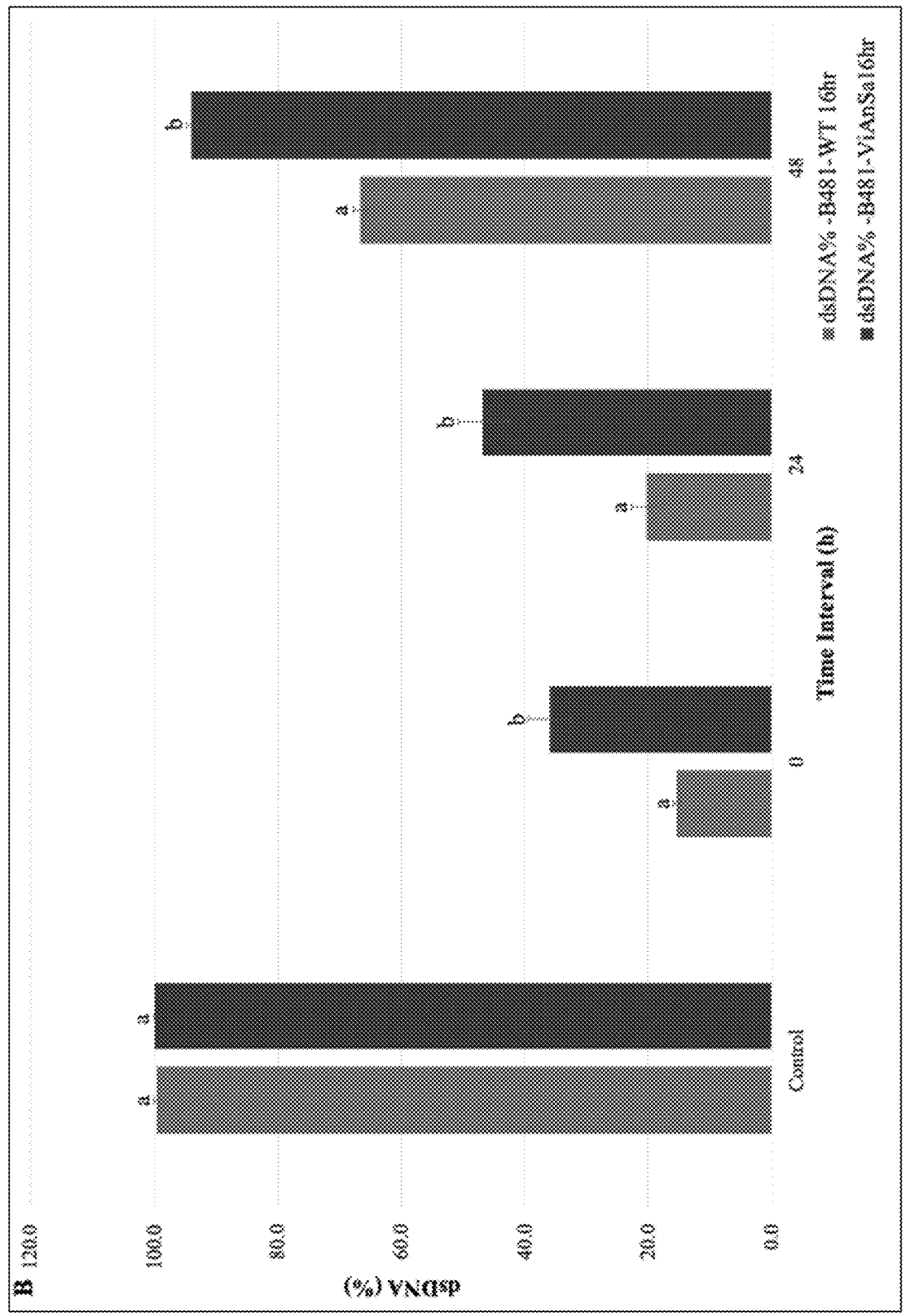
FIG. 5B is a chart showing percentages of double stranded DNA in *F. diplosiphon* wild type (B481-WT) and transformant (B481-ViAnSa) strains after exposure to UVB radiation (3.0 W m$^{-2}$ (~8.0 μmol m$^{-2}$s$^{-1}$)) for 16 h. Different letters above standard error bars indicate significance between percentages (p<0.05).

Given that cyanobacteria use solar energy for essential energy-dependent processes, harmful UV-B radiation affects several physiological and biochemical processes such as photosynthesis, growth, survival, cell differentiation, genome integrity and total lipid profiles. Therefore, we evaluated the efficacy of the transformant under UV-B conditions at an intensity of 3.0 W m$^{-2}$ at the surface of the cell culture. Our results revealed significantly high UV-B tolerance in the transformant radiated for 20 to 160 m. While a significant reduction ($p<0.05$) in growth of B481-WT was observed even at 20 m of UV-B exposure, the transformant (B481-ViAnSa) showed no significant reduction of growth at exposure time of 40-160 min (Table 1).

reliable analysis of DNA strand breaks in UVt samples since the amount of DNA damage in treated cells is expressed by the difference in fluorescence intensities. Using this assay, we detected significantly higher ($p<0.05$) DNA damage in both B481-WT and B481-ViAnSa strains exposed to UV-B at 12 and 16 h (FIG. 5) compared to the untreated control (sample-ds). While our results indicated a significant reduction ($p<0.05$) in the dsDNA of both strains exposed to UV-B, the transformant exhibited significantly less dsDNA breakages compared to wildtype. In addition, significantly high ($p<0.05$) dsDNA of 60.3, 70.2 and 98.1% were observed in B481-ViAnSa compared to B481-WT (50.4, 55.6, and 81.5%) at 0, 24, 48 h post-UV-B irradiation. Interestingly, we noted significantly higher ($p<0.05$) dsDNA recovery in B481-ViAnSa (98.1%) compared to B481-WT (81.5%) after 48 h (FIG. 5B).

These results show that higher photolyase activity results in more efficient DNA repair in the transformant. In addition, this strain exhibited a significantly higher ($p<0.05$) percentage of dsDNA at 16 h of UV-B radiation. Comparison of gene transcription in the transformant and DNA damage showed an inverse correlation. While the phr A gene overexpression in the transformant was significantly high ($p<0.05$) compared to the wildtype, DNA damage as indicated by FADU assay was low. These results indicate that the overexpression of the photolyase gene reduced thymine dimers caused by UV-B.

TABLE 1

Pairwise comparison of mean growth differences between the wildtype (B481-WT) and (B481-ViAnSa) *Fremyella diplosiphon* strains.
Pairwise Comparisons Mean Difference

| Variable | (i) Strains | (j) Strains | Mean Difference | Std. Error | Significance | 95% Confidence Interval for Difference | |
|---|---|---|---|---|---|---|---|
| | | | | | | Lower Bound | Upper Bound |
| Control | B481-phrA | B481-WT | 0.05 | 0.002 | <.001 | 0.046 | 0.054 |
| | B481-WT | B481-phrA | −.050* | 0.002 | <.001 | −0.054 | −0.046 |
| 20 min | B481-phrA | B481-WT | 0.168 | 0.002 | <.001 | 0.164 | 0.172 |
| | B481-WT | B481-phrA | −0.168 | 0.002 | <.001 | −0.172 | −0.164 |
| 40 min | B481-phrA | B481-WT | 0.162 | 0.002 | <.001 | 0.159 | 0.166 |
| | B481-WT | B481-phrA | −0.162 | 0.002 | <.001 | −0.166 | −0.159 |
| 80 min | B481-phrA | B481-WT | .209* | 0.002 | <.001 | 0.205 | 0.213 |
| | B481-WT | B481-phrA | −.209* | 0.002 | <.001 | −0.213 | −0.205 |
| 160 min | B481-phrA | B481-WT | .157* | 0.002 | <.001 | 0.154 | 0.161 |
| | B481-WT | B481-phrA | −.157* | 0.002 | <.001 | −0.161 | −0.154 |

Based on estimated marginal means
*The mean difference is significant at the .05 level.

Interestingly, we also observed a significantly rapid growth recovery of the B481-ViAnSa strain compared to B481-WT (FIG. 3). Furthermore, irradiation of B481-ViAnSa for 20 min significantly ($p<0.05$) increased growth rate over a 14-day period compared to the non-irradiated transformant, indicating exceptional growth performance under UV stress.

Figure 4:
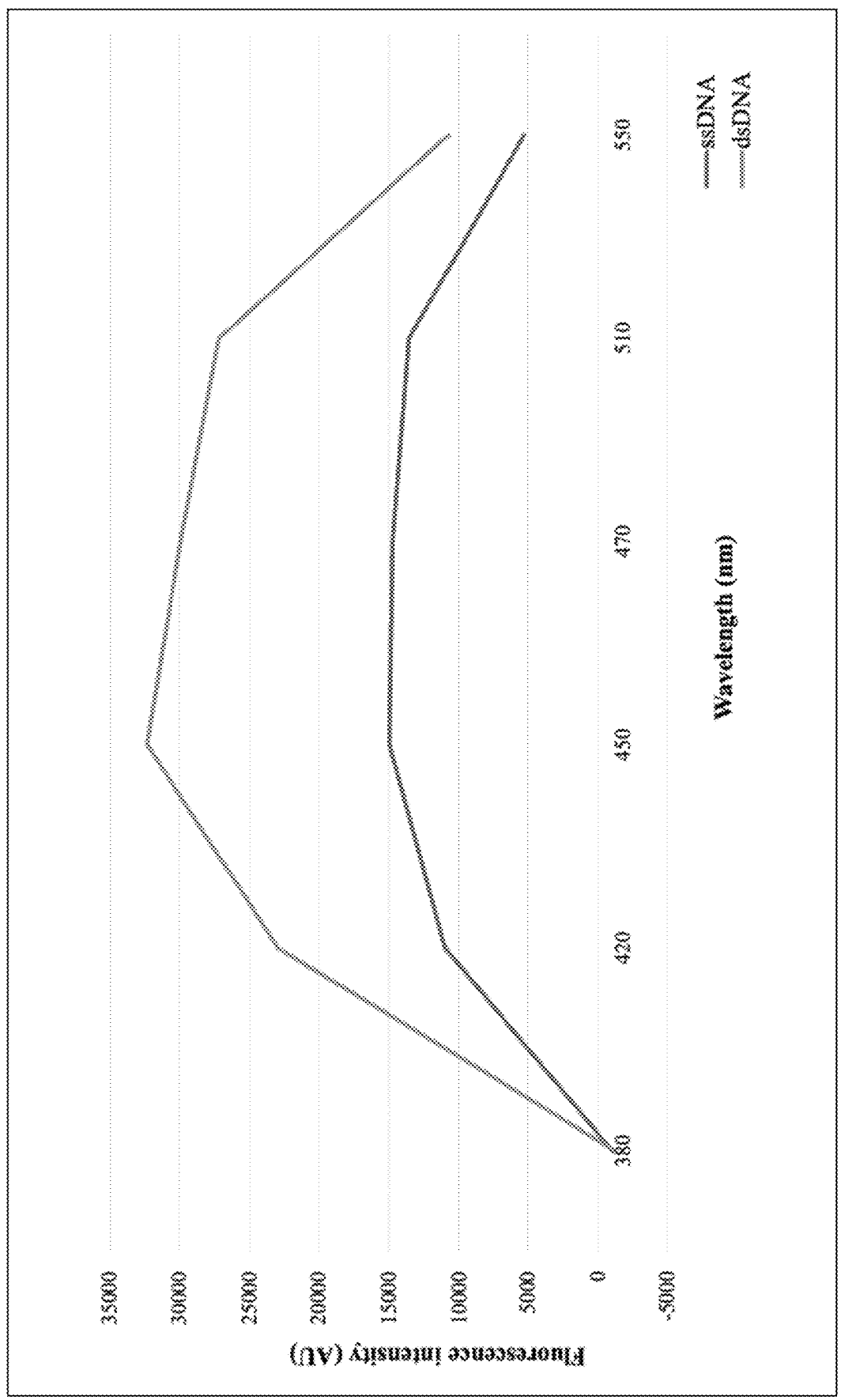
FIG. 4 is a chart showing fluorescence excitation of *F. diplosiphon* DNA-bound Hoechst 33258. Emission data (emission peak 450 nm) were obtained using the maximum wavelength of the excitation peak at 343 nm. The dsDNA was not subjected to alkaline unwinding while ssDNA was subjected to complete alkaline unwinding.
Figure 6A:
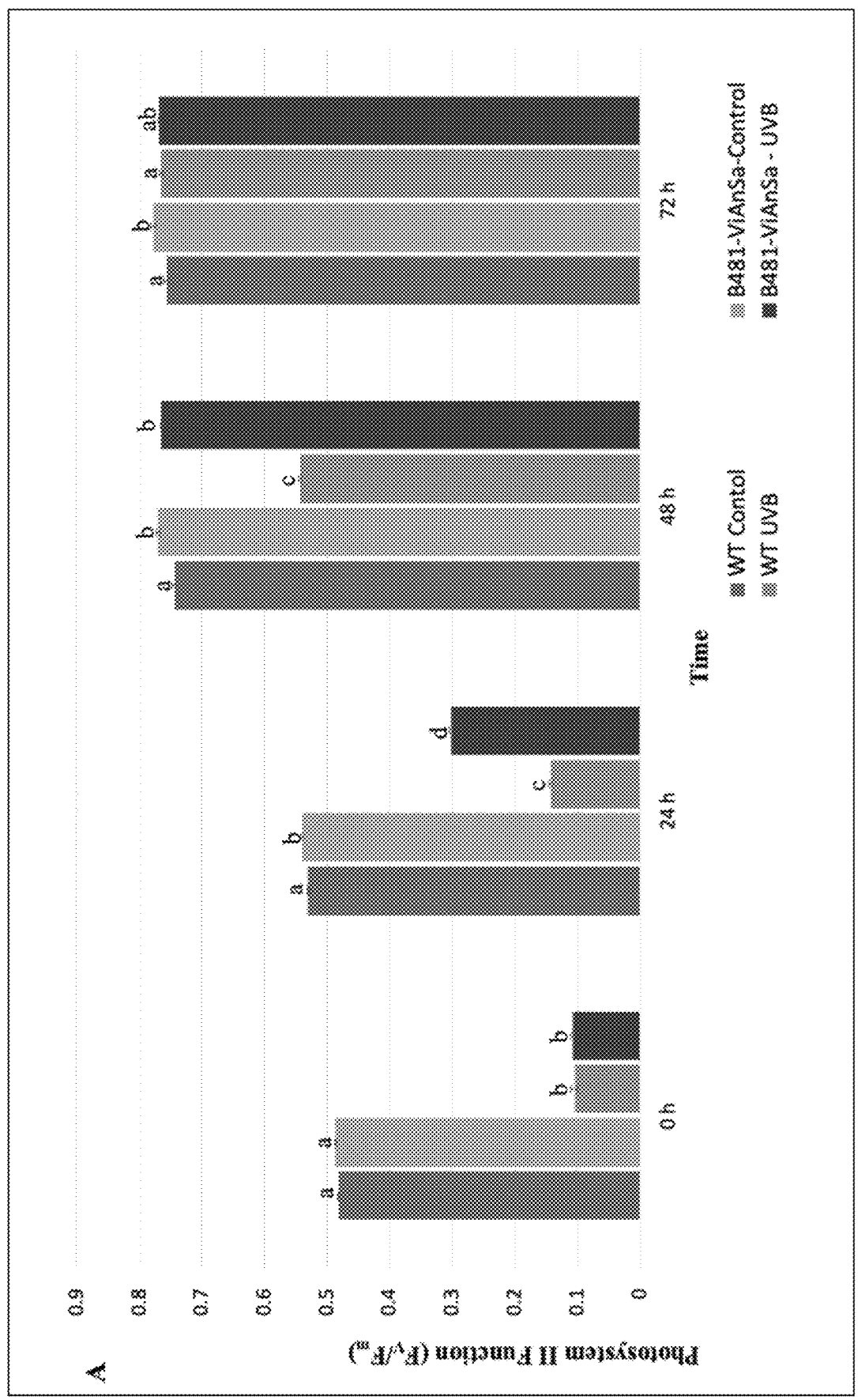
FIG. 6A is a chart showing evaluation of photosystem II activity in *F. diplosiphon* B481-WT and B481-ViAnSa strains after 12 h UVB radiation. Different letters above error bars indicate significance differences (p<0.05).
Figure 6B:
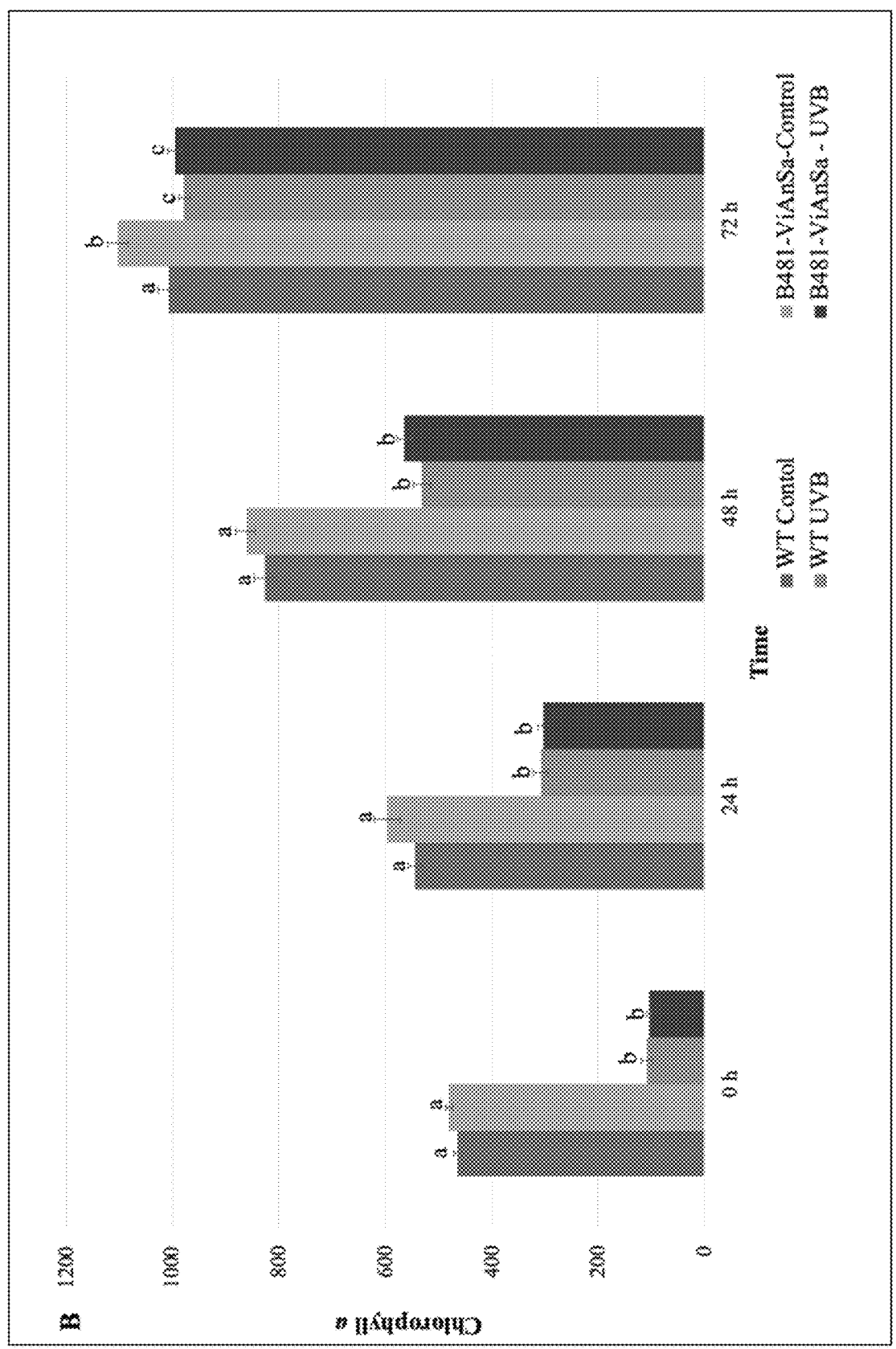
FIG. 6B is a chart showing evaluation of chlorophyll a content in *F. diplosiphon* B481-WT and B481-ViAnSa strains after 12 h UVB radiation. Different letters above error bars indicate significance differences (p<0.05).

Comparison of DNA Strand Breakages in the Transformant and Wildtype *Fremyella diplosiphon* Strains FADU assay, an accurate and powerful method for quantitative analysis of DNA damage, was used to measure DNA strand breaks in the transformant engineered with the phr A (B481-ViAnSa). Quantification of dsDNA damage detected by fluorescence analysis of the fluorochrome bound DNA revealed maximal fluorescence at 450 nm while it was lower in ssDNA (FIG. 4). The difference between upper and lower fluorescence limit of ds- and ss-samples provided a more Evaluation of Photosystem II Activity and Chlorophyll a Content in the Transformant, B481-ViAnSa The ratio of variable and maximum fluorescence (Fv/Fm) of the dark-adapted chlorophyll a fluorescence parameter was used to measure photochemical efficiency of photosystem II reaction centers. Comparison of photosystem II activity and chlorophyll a content between the wildtype and transformant strains did not reveal significant differences (FIG. 6). However, we noticed a significant difference ($p<0.05$) in the photosystem II (PSII) recovery rate of the UV-treated transformant compared to the wildtype. While the transformant PSII recovered in 48 h following UV-B radiation at an intensity of 3.0 W m$^{-2}$ for 1 h, the wildtype strain took 72 h, indicating enhanced photolyase gene activity in the transformant contributing to UV stress tolerance.

Fatty Acid Methyl Ester Composition in UV-B Irradiated and Non-Irradiated *Fremyella diplosiphon* Strains, B481-ViAnSa and B481-WT

*F. diplosiphon* possesses valuable biodiesel qualities, which can maximize biofuel production. Hence, we compared the high-value saturated and unsaturated FAMEs in the transformant to the wildtype strain. Methyl palmitate, the methyl ester of hexadecenoic acid (C16:0), was found to be the most dominant FAME component, accounting for 53.43% and 51.69% in B481-ViAnSa and B481-WT, respectively. Methyl octadecenoate (C18:0), the second abundant FAME, accounted for 30.12% and 33.02% in B481-ViAnSa and B481-WT respectively. This was followed by methyl octadecenoate (C18:1), which accounted for 22% in B481-ViAnSa and 23.02% in B481-WT. Additionally, we detected methyl tetradecanoate (C14:1), methyl hexadecanoate (C16:1), and methyl octadecadienoate (C18:2) in both strains (Table 2).

TABLE 2

Quantitative composition of fatty acid methyl esters in transesterified lipids of non-irradiated and UVB radiated *F. diplosiphon* wild type (WT) and transformant (B481-ViAnSa) strains.

| | Nonirradiated | | UVB Irradiated | |
|---|---|---|---|---|
| FAMEs Type | B481-ViAnSa | B481-WT | B481-ViAnSa | B481-WT |
| Methyl palmitate (C16:0) | 53.43% | 51.69% | 42.47% | 41.74% |
| Methyl octadecanoate (C18:0) | 30.12% | 33.02% | 23.33% | 24.18% |
| Methyl octadecanoate (C18:1) | 22% | 23.02% | 15.99% | 17.05% |
| methyl tetradecanoate (C14:1) | 5.19% | 5.07% | 1.18% | 2.07% |
| Methyl hexadecanoate (C16:1) | 4.76% | 4.59% | 0.87% | 0.81% |
| Methyl octadecadienoate (C18:2) | 3.01% | 3.13% | 0.91% | 0.78% |

Interestingly, UV-B radiation significantly reduced ($p<0.05$) the percentage of all FAME components, including methyl palmitate, which was reduced by 20.51% and 19.25% in B481-ViAnSa and B481-WT respectively (Table 2). Due to the exposure of cultures to simulated UV-B radiation for 4 continuous hours, a reduction of FAMEs is expected. However, we observed significantly higher ($p<0.05$) amounts of saturated FAMEs in both strains irradiated with UV-B when compared to the untreated control.

In summary, our results indicate that overexpression of the phrA gene enhanced *F. diplosiphon* UV stress tolerance, with enhanced PS II reversal rate and no negative impact on lipids. Considering future projections of increased UV-B radiation reaching the earth's surface due to environmental pollution and depletion of the ozone layer, this invention paves the way for cultivating *F. diplosiphon* in large-scale outdoor systems.

It will be appreciated by those skilled in the art that changes could be made to the preferred embodiments described above without departing from the inventive concept thereof. It is understood, therefore, that this invention is not limited to the particular embodiments disclosed, but it is intended to cover modifications within the spirit and scope of the present invention as outlined in the present disclosure and defined according to the broadest reasonable reading of the claims that follow, read in light of the present specification.

The invention claimed is:

1. A recombinant *Fremyella diplosiphon* cyanobacterium comprising at least one expression plasmid comprising the nucleotide sequence corresponding to SEQ. ID. NO. 3, wherein the recombinant *Fremyella diplosiphon* cyanobacterium has a higher UV tolerance as compared to wild-type *Fremyella diplosiphon* cyanobacterium.

2. A recombinant *Fremyella diplosiphon* cyanobacterium comprising at least one expression plasmid comprising the nucleotide sequence corresponding to SEQ. ID. NO. 3, wherein the recombinant *Fremyella diplosiphon* cyanobacterium is more resistant to UV-induced DNA damage as compared to wild-type *Fremyella diplosiphon* cyanobacterium.

3. A recombinant *Fremyella diplosiphon* cyanobacterium comprising at least one expression plasmid comprising the nucleotide sequence corresponding to SEQ. ID. NO. 3, wherein the recombinant *Fremyella diplosiphon* cyanobacterium shows a higher dsDNA recovery following DNA damage as compared to wild-type *Fremyella diplosiphon* cyanobacterium.

* * * * *